(12) United States Patent
Geier et al.

(10) Patent No.: US 6,347,543 B1
(45) Date of Patent: Feb. 19, 2002

(54) MEASURING SENSOR AND METHOD FOR ITS FABRICATION

(75) Inventors: Heinz Geier, Leonberg; Helmut Weyl, Schwieberdingen; Hans-Martin Wiedenmann, Stuttgart; Karl-Hermann Friese, Leonberg, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/434,667

(22) Filed: Nov. 5, 1999

(30) Foreign Application Priority Data

Nov. 5, 1998 (DE) .......................................... 198 50 959

(51) Int. Cl.$^7$ ..................... G01N 27/04; G01N 27/407; H01C 7/00; G01M 15/00
(52) U.S. Cl. .................... 73/23.31; 73/31.05; 73/23.32; 338/34; 338/230; 204/426; 204/424; 204/422; 204/94; 29/878
(58) Field of Search .............................. 73/23.31, 23.32, 73/31.01, 31.05; 204/424, 426; 338/34, 229, 230; 422/94; 123/672; 29/878

(56) References Cited

U.S. PATENT DOCUMENTS

| | | | | |
|---|---|---|---|---|
| 4,206,173 A | * | 6/1980 | Yamaguchi et al. | 422/98 |
| 4,310,401 A | * | 1/1982 | Stahl | 204/195 S |
| 5,039,972 A | * | 8/1991 | Kato et al. | 338/34 |
| 5,139,639 A | * | 8/1992 | Holleboom | 204/427 |
| 5,602,325 A | * | 2/1997 | McClanaham et al. | 73/23.31 |
| 5,616,825 A | * | 4/1997 | Achey et al. | 73/23.31 |
| 5,739,414 A | * | 4/1998 | Paulus et al. | 73/23.31 |
| 5,817,920 A | * | 10/1998 | Kuisell et al. | 73/23.31 |
| 5,955,656 A | * | 9/1999 | Graser et al. | 73/23.31 |
| 6,032,514 A | * | 3/2000 | Weyl et al. | 73/31.05 |
| 6,082,175 A | * | 7/2000 | Yoshikawa et al. | 73/23.31 |
| 6,164,120 A | * | 12/2000 | Friese et al. | 73/23.2 |
| 6,223,583 B1 | * | 5/2001 | Friese et al. | 73/23.31 |

FOREIGN PATENT DOCUMENTS

DE 197 07 458 8/1998

* cited by examiner

Primary Examiner—Hezron Williams
Assistant Examiner—David J. Wiggins
(74) Attorney, Agent, or Firm—Kenyon & Kenyon (57) ABSTRACT

A measuring sensor, in particular, for determining the oxygen content in exhaust gases of internal combustion engines, includes a ceramic molding arranged in a metal housing for the accommodation of a sensor element, in particular, planar, the sensor element being sealed by a seal element made of warm-deformable temperature-resistant material. The molded housing is designed in one piece and has a cylindrically shaped longitudinal hole on the connector side, around the sensor element, and the seal element is compressed between a first compressing element on the measuring-gas side and a second compressing element on the connector side, such that it tightly encloses the sensor element and hermetically seals the sensor element with respect to the molded housing.

46 Claims, 5 Drawing Sheets

MEASURING SENSOR AND METHOD FOR ITS FABRICATION

FIELD OF THE INVENTION

The present invention relates to a measuring sensor and a method for fabricating the measuring sensor.

BACKGROUND INFORMATION

German Published Patent Application No. 197 07 458 describes a measuring sensor. This document further describes a joining method for the measuring sensor. In the measuring sensor, a molded ceramic housing includes two parts, namely, a ceramic molding on the measuring-gas side and a ceramic molding on the connector side, which are arranged lying axially one behind the other. Between the two ceramic moldings, a cavity is formed in which a warm-deformable metallic seal element is inserted. The two parts of the ceramic housing serve as compressing elements in the insertion operation. The seal element in the measuring sensor can include a ductile metal body made of copper, aluminum, palladium, nickel, silver, or an alloy of these metals with additives such as graphite, boron nitride, talc, bentonite, kaolin, or the metal body is a composite body having a core with a surface coating on one side or both sides. Alternatively, the seal element can also be a metal solder into which additives such as graphite, boron nitride, talc or a mixture of these additives are admixed.

SUMMARY OF THE INVENTION

It is an object of the present invention to provide a measuring sensor and a method for its fabrication such that no crack-initiating stresses arise in the component upon the occurrence of temperature gradients or of temperature intervals.

Reliable hermetic sealing of the inserted sensor element against gas and gasoline is achieved according to the present invention because the molded housing is designed in one piece and exhibits an axially symmetric and cylindrically shaped longitudinal hole on the connector side, around the sensor element, and/or a metal shell pushed onto the molded housing in gastight fashion on the connector side, and the seal element is inserted in the longitudinal hole and/or metal shell between a first compressing element on the measuring-gas side and a second compressing element on the connector side such that it tightly encloses the sensor element in the molded housing or, respectively, in the metal shell and hermetically seals the sensor element with respect to the molded housing and/or the metal shell. Damage to the molded ceramic housing and cracking of the molded ceramic housing upon insertion are averted because, for example, the molded ceramic housing no longer serves as a compressing element.

Thus, according to the present invention, the sensor element is inserted into a molded ceramic housing or into a metal shell pushed onto a ceramic molding to construct the joint, subject to the conditions of the joining operation.

The fabrication method according to the present invention, with which a measuring sensor according to the present invention can be fabricated, includes the following steps:

A. The first compressing element is inserted into the longitudinal hole of the molded ceramic housing or into the metal shell with inserted sensor element;

B. The seal element is laid on first compressing element and around the sensor element; the second compressing element is arranged (laid) on top of it;

C. The workpiece, preassembled to this point, is placed in a temperature-resistant workpiece carrier;

D. The workpiece carrier with inserted workpiece is heated in a furnace, preferably in air, to a particular temperature for a particular length of time;

E. The workpiece carrier with inserted workpiece is removed from the furnace;

F. With an external ram, the second compressing element is inserted warm, at a certain temperature, preferably in air, onto and into the seal element inside the longitudinal hole of the molded housing or inside the metal shell, until the ram makes contact with the molded housing or the metal shell.

A reliable and economical method for the hermetic sealing of sensor elements in the sensor housing is provided by the fabrication method according to the present invention. Warm insertion makes possible the use of stable glasses with relatively high transformation temperature at a low joining temperature, which results in, for example, no excessive thermal stress for the sensor element. Further, metal-containing seal materials can be used, which have significant advantages over pure glass castings.

The first compressing element is preferably a powder compact made of temperature-resistant material, preferably with good frictional qualities, such as, for example, steatite, talc, graphite, boron nitride, or copper. Alternatively, the first compressing element is made of glass, glass-ceramic, oxide-ceramic with the addition, as appropriate, of organic binders, placed as loose-poured powder or granules, as a compact, presintered, as appropriate, and/or as a cast film; the first compressing element is preferably inserted cold to fix the sensor element in place.

The seal element is made of warm-deformable, temperature-resistant material, preferably of glass and/or metal, advantageously copper, with the addition, as appropriate, of organic binder and other reducing agents, placed as loose-poured powder, granules or compound ("panat"), as a compact, presintered as appropriate, and/or as a cast film.

The second compressing element is made of ceramic powder, high-melting glass powder and/or metal powder, alternatively of steatite or talc, which are preferably not presintered and to which organic binding agents and or compacting aids are added, or, further alternatively, of zirconium oxide or, respectively, Ba—Al silicate glass, which is preferably sintered. The end face of the second compressing element may have projections, protruding toward the seal element, with which the second compressing element can be anchored in the seal element.

In the joining operation (steps A–F), pores in the seal element are eliminated or open pores are closed. As the temperature is raised during the joining operation, non-presintered compressing elements are presintered to the extent that they acquire sufficient strength for the compression of the seal element.

The external ram is preferably split, and a section of the external ram set on the part being joined, which section is preferably made of sintered $Al_2O_3$ or $ZrO_2$ ceramic, is co-heated to the joining temperature. Then the external ram is preferably pushed until stopped by the molded ceramic housing or the metal shell, so that the second compressing element makes flush contact with the connector-side end surface of the molded ceramic housing or of the metal shell.

DETAILED DESCRIPTION

First, some of the components of a measuring sensor according to the present invention are explained with reference to FIG. 1.

Figure 1:
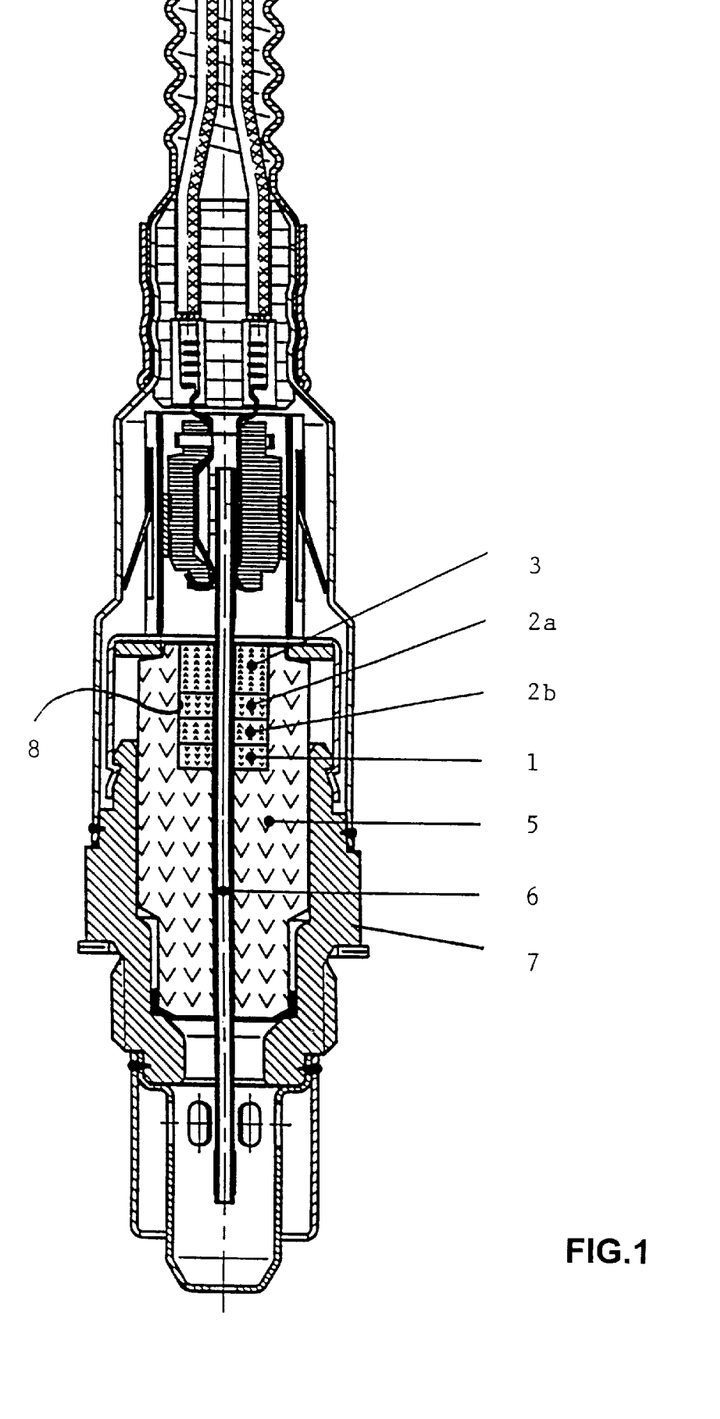
FIG. 1 shows an embodiment of a measuring sensor fabricated with the steps of the method according to the present invention.

The measuring sensor shown in FIG. 1 is an electrochemical measuring sensor for determining the oxygen content in exhaust gases of internal combustion engines. A planar, wafer-shaped sensor element 6 is located inside a metal housing 7. Arranged in housing 7 is a longitudinal hole provided with annular shoulders with which a molded ceramic housing 5 sitting in the longitudinal hole makes contact. Molded housing 5 is made in one piece and has, on the connector side, a cylindrical longitudinal hole 8 about the central longitudinal axis of planar sensor element 6. Sitting in this longitudinal hole 8 of molded ceramic housing 5, as viewed from its bottom surface on the measuring-gas side to its connector-side opening, are a first compressing element 1, a seal element 2b, 2a, and a second compressing element 3 making flush contact with molded ceramic housing 5. Some further features of the measuring sensor shown in FIG. 1 are described, for example, in German Published Patent Application No. 197 07 458.

Figure 2A:
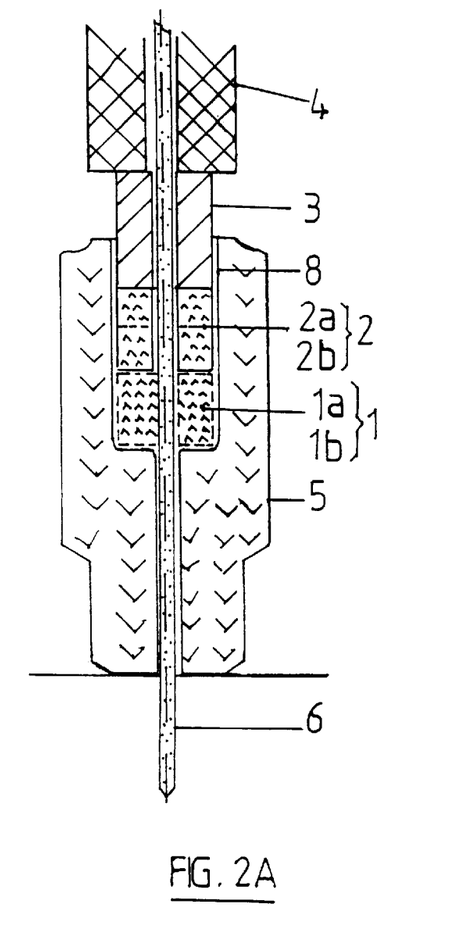
FIG. 2A shows an assembly before a joining operation according to the present invention.
Figure 2B:
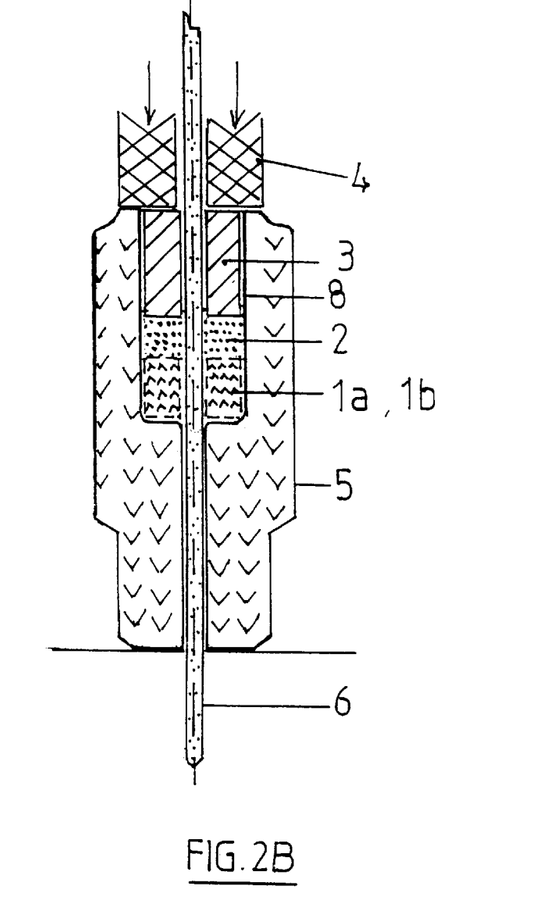
FIG. 2B shows the assembly after the joining operation according to the present invention.

First to Third Exemplary Embodiments of the Fabrication Method (FIGS. 2A, 2B):

In FIGS. 2A and 2B, molded housing 5, made of sintered steatite ceramic, with sensor element 6 inserted in it, is held by a temperature-resistant workpiece carrier (not shown) made of, for example, oxide ceramic. The components to be joined, i.e., first compressing element 1a, 1b, seal element 2, 2a, 2b, and second compressing element 3, lie in hole 8 of molded ceramic housing 5 around sensor element 6; second compressing element 3 is attached to an external, preferably split, ram 4, which is preferably made of sintered $Al_2O_3$ or $ZrO_2$ ceramic and is, as explained in what follows, co-heated to the joining temperature.

First Exemplary Embodiment

First compressing element 1a, which is an unsintered steatite compact with 2% organic binder, is first inserted cold. The ram and insertion step provided for the purpose are not illustrated.

Seal element 2, made of warm-deformable, temperature-resistant material, preferably a glass-Cu compound compact consisting of 70 vol. % Na borosilicate glass, 30 vol. % Cu powder (copper grindings), and 5 wt. % dextrin (coefficient of thermal expansion $9\times10^{-6}$ $K^{-1}$), is then inserted. Second compressing element 3 is inserted over it. The workpiece assembled to this point, held in the temperature-resistant workpiece carrier, is heated in a furnace, preferably in air, to a temperature below 1000° C., preferably 850° C. Organic additives can create a reducing atmosphere at the joint.

Next, the workpiece is removed from the furnace with the workpiece carrier, and temperature-resistant external ram 4 is used to insert second compressing element 3 warm, in air, until external ram 4 is stopped by the connector-side end surface of the molded ceramic housing 5 and seal element 2 tightly encloses sensor element 6 and forms a hermetic seal against the molded ceramic housing. Second compressing element 3, like first compressing element 1a, can be an unsintered steatite compact with 2% organic binder (PVA).

FIG. 2B shows the condition of the assembled components after the warm insertion of second compressing element 3. It is evident that the axial length of both first compressing element 1, seal element 2, and also second compressing element 3 has been reduced by the joining operation. The glass-Cu compound compact of seal element 2 penetrates into the gaps left by second compressing element 3 between sensor element 6 and molded ceramic housing 5, and, in this way, second compressing element 3 is anchored in seal element 2 and sensor element 6 is hermetically sealed against molded ceramic housing 5. Pores in seal element 2 are eliminated or open pores are at least closed during the joining operation.

Second Exemplary Embodiment

In the second exemplary embodiment, in contrast to the first exemplary embodiment, first compressing element 1b (shown dashed) is inserted not cold but warm and not until the operation of inserting second compressing element 3 into seal element 2. It is again a steatite compact as in the first exemplary embodiment. Seal element 2 can be identical with that of the first exemplary embodiment or, alternatively, can be made of Li borosilicate glass with coefficient of thermal expansion $7.7\times10^{-6}$ $K^{-1}$. The other features are identical with those of the first exemplary embodiment. After the compression step, seal element 2 fills the gaps left by first compressing element 1 and second compressing element 3 between sensor element 6 and molded ceramic housing 5, as shown in FIG. 2B, so that seal element 2 tightly encloses sensor element 6 and seals it hermetically against molded 5. Here again, pores in the seal element are eliminated and/or open pores are closed during the joining operation.

Third Exemplary Embodiment

In contrast to the first and second exemplary embodiments, here seal element 2 according to FIG. 2A includes two components (dashed parting line), namely a first component 2b, which is a compact of Cu powder (copper grindings) with 5% dextrin added, in contact with first compressing element 1a or 1b, and a second component, including a compact of Li borosilicate glass with coefficient of thermal expansion $7.7\times10^{-6}$ $K^{-1}$ with the addition of 5% dextrin, adjacent on the connector side. Further, second compressing element 3 is a steatite compact presintered for two hours at 600° C. After the warm insertion of the second compressing element 3, both components 2a and 2b of the seal elements fuse, as shown in FIG. 2B, into one seal element 2, which fills the gaps between first compressing element 1a or, respectively, 1b, sensor element 6 and molded ceramic housing 5 and which fills the gaps between second compressing element 3, sensor 6, and molded ceramic housing 5 in such a way that seal element 2 tightly encloses sensor element 6 and seals sensor element 6 hermetically against molded ceramic housing 5. Upon warm insertion, the glass of second component 2a penetrates into the Cu compact of first component 2b of the seal element.

Figure 3A:
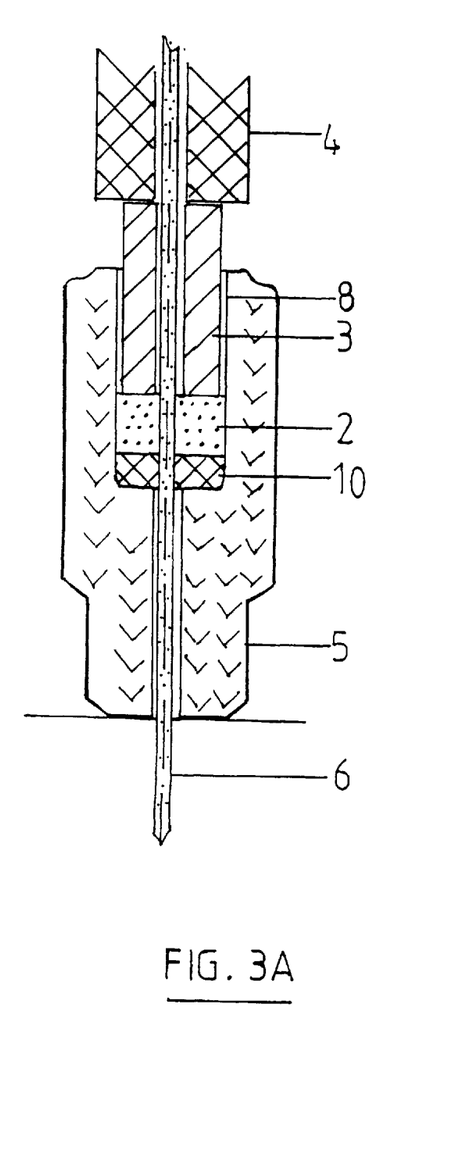
FIG. 3A shows an embodiment of the assembly before the joining operation according to the present invention.
Figure 3B:
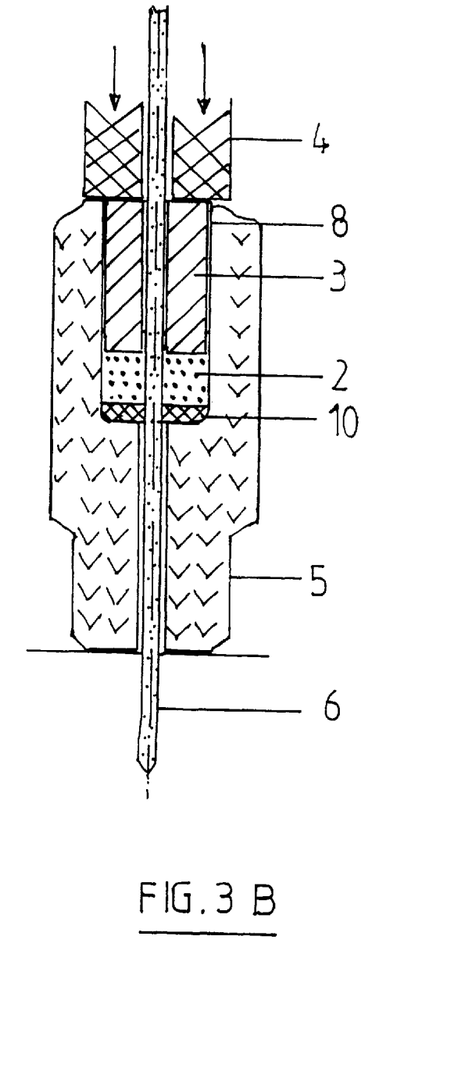
FIG. 3B shows the embodiment of FIG. 3A after the joining operation according to the present invention.

Fourth Exemplary Embodiment (FIGS. 3A, 3B)

As FIG. 3A shows, the fourth exemplary embodiment differs from the first three exemplary embodiments described above in that first compressing element 10, made as a cast seal film with 40–70 vol. % organic binder (for example, polyvinyl butyral) filled with ceramic powder, such as, for example, $Al_2O_3$ or $ZrO_2$, and/or with high-melting glass and/or with graphite and/or with boron nitride or, respectively, reinforced with fibers and or fabric and/or braids, is first inserted cold into longitudinal hole 8 of molded ceramic housing 5. The other features and steps of the method can be identical to the steps of the method previously described for the first three exemplary embodiments. Sensor element 6 is initially fixed in place by the cold insertion of cast seal film 10.

As FIG. 3B shows, the cast film of first compressing element 10, additionally deformed by the warm insertion operation, hermetically seals sensor element 6, in addition to seal element 2, with respect to molded ceramic housing 5. FIG. 3B shows, furthermore, that after the warm insertion of second compressing element 3, seal element 2 fills the gaps remaining between second compressing element 3 and sensor element 6 as well as molded ceramic housing 5 because of the insertion of second compressing element 3, and thus anchors second compressing element 3 in seal element 2.

Figure 4A:
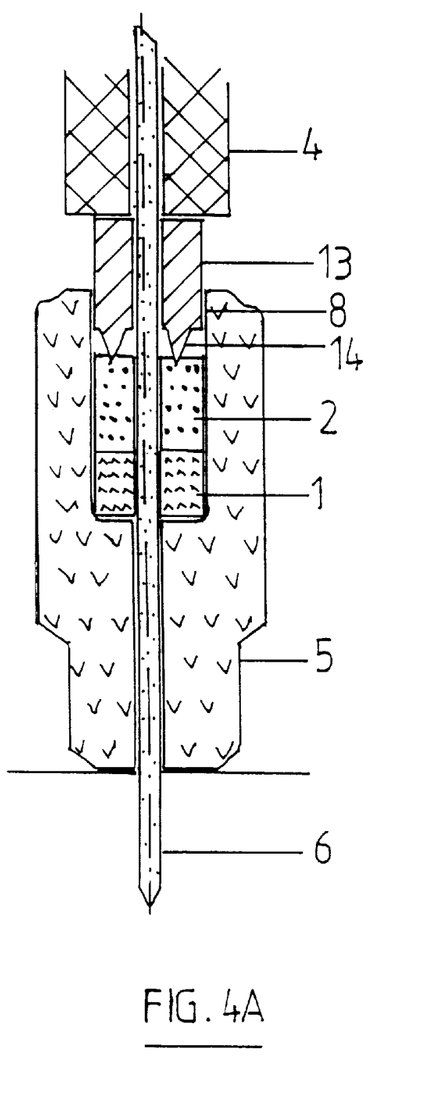
FIG. 4A shows another embodiment of the assembly before the joining operation according to the present invention.
Figure 4B:
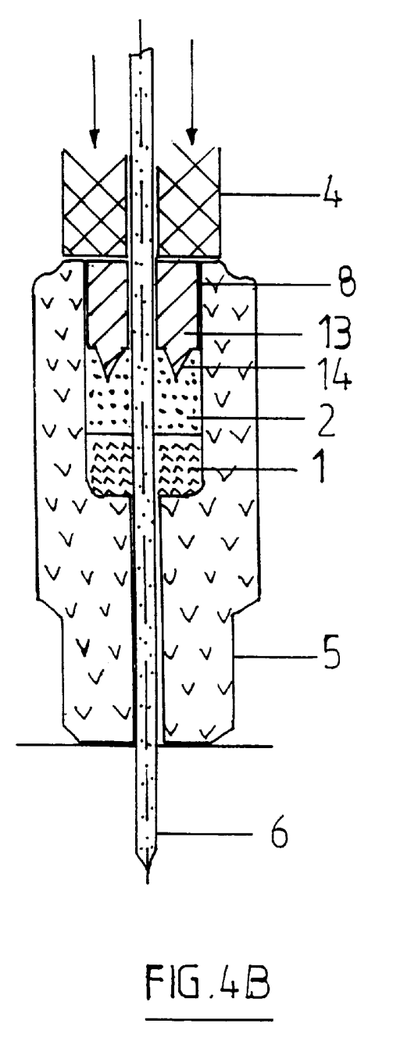
FIG. 4B shows the embodiment of FIG. 4A after the joining operation according to the present invention.

Fifth Exemplary Embodiment (FIGS. 4A, 4B)

First compressing element 1 is a steatite compact as in the first exemplary embodiment and, as there, is inserted cold. Seal element 2 is a compact of Cu powder (copper grindings) with 5% dextrin. Second compressing element 13 is made of sintered $ZrO_2$ ceramic and has, on its end face, turned toward seal element 2, projections 14 extending to seal element 2. Projections 14 serve to anchor second compressing element 13 in seal element 2. This is illustrated in FIG. 4B. The insertion operation or joining operation, in which second compressing element 13 is inserted with external ram 4, may be performed at 950° C.

The embodiments described above have in common that, upon the temperature increase during the joining operation, non-presintered compressing elements are presintered to the extent that they acquire sufficient strength for the compression of the seal element.

Figure 5:
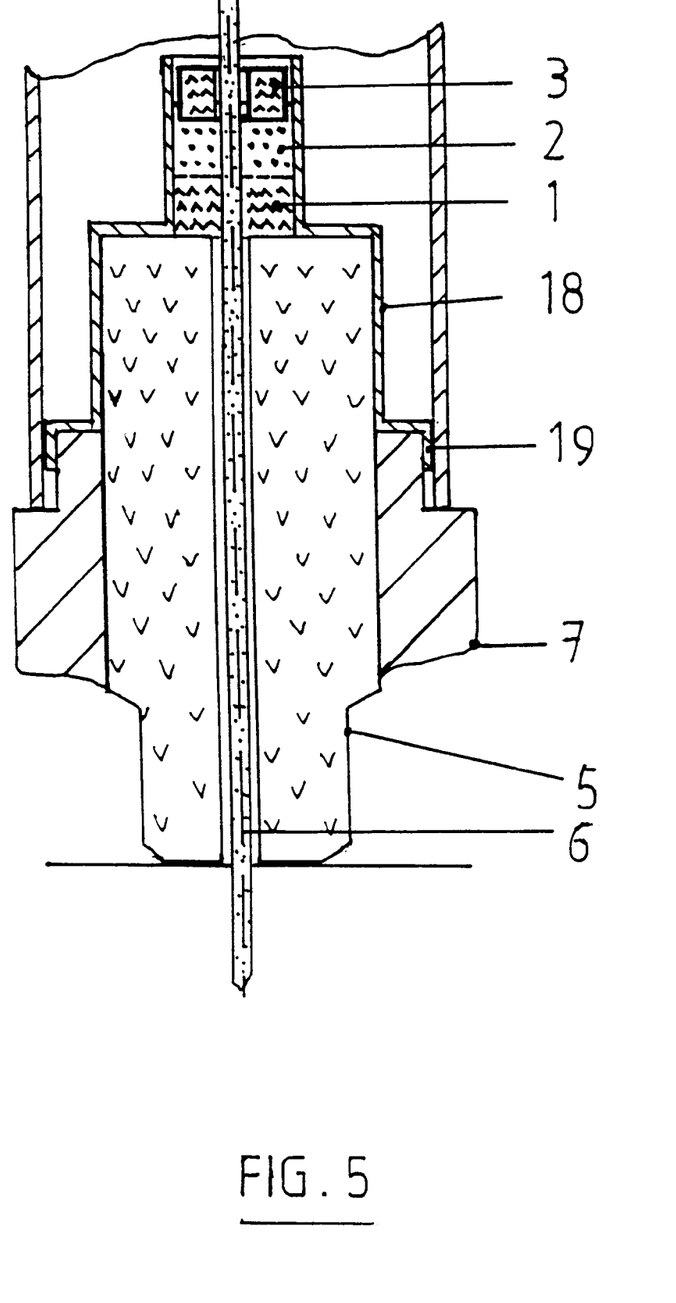
FIG. 5 shows another embodiment of the measuring sensor according to the present invention.

It should be noted that in a further embodiment of the measuring sensor according to the present invention shown in FIG. 5, a metal shell 18 is pushed onto molded ceramic housing 5 in gastight fashion on the connector side. The gastight weld with the external metal shell is identified by reference numeral 19. In the joining operation, second compressing element 3 is then inserted into metal shell 18 until the connector-side end face of second compressing element 3 is substantially flush with the connector-side end face of metal shell 18. Here again, second compressing element 3, 13 is inserted before the heat treatment.

In what follows, general advantages of the metal-containing seal materials preferably used in the present invention as, for example, the glass-Cu compound compact used in seal element 2 according to FIGS. 2a and 2b, are listed in comparison with pure glass castings. In that suitable substances and mixture ratios are selected for such a metal-containing seal material, its thermal expansion is adapted to that in the other joint elements. The use of glass with a low melting point is possible because glass with a low thermal expansion can be used. Residual stresses are relieved by embedded metal particles, which are ductile or, respectively, plastically deformable at elevated temperature. In this way, crack formation and crack propagation are prevented or strongly limited. The use of low-cost steatite ceramic for the molded ceramic housing is possible as a result. The metal-containing seal material has improved adhesion to the sensor element because of the limited solid-state reaction of metal and zirconium dioxide. Also as a result, crack formation between the fused material and the sensor element is reliably limited, particularly in the edge region.

Improved frictional action and improved plastic deformation are achieved by the warm insertion of the metal-containing seal material. As a result, the joining temperature is reduced and excessive thermal stress is averted. On the whole, the features according to the present invention make possible a reliable and economical fabrication operation for the hermetic sealing of, in particular, planar sensor elements in the sensor housing, that is, in the molded ceramic housing. The proposed warm insertion makes it possible to use stable glasses with relatively high transformation temperature at a low joining temperature, which results in no excessive thermal stress for the sensor element.

What is claimed is:

1. A measuring sensor, comprising:
    a metal housing;
    a seal element including a warm-deformable temperature-resistant material;
    a sensor element sealed by the seal element;
    a device including at least one of:
        a ceramic molded housing designed in one piece arranged in the metal housing, the ceramic molded housing having a connector side and a measuring-gas side, the ceramic molded housing accommodating the sensor element, the ceramic molded housing including a longitudinal hole disposed around the sensor element, the longitudinal hole being disposed toward the connector side and being axially symmetric and cylindrically-shaped, and
        a metal shell pushed onto the ceramic molded housing in a gastight manner on the connector side,
    a first compressing element disposed toward the measuring-gas side; and
    a second compressing element, disposed toward the connector side,
    wherein the seal element is in at least one of the longitudinal hole and the metal shell, and
    wherein the seal element is compressed between the first compressing element and the second compressing element such that, the seal element tightly encloses the sensor element in at least one of the ceramic molded housing and the metal shell, and hermetically seals the sensor element with respect to at least one of the ceramic molded housing and the metal shell.

2. The measuring sensor according to claim 1, wherein the measuring sensor determines an oxygen content in an exhaust gas of an internal combustion engine.

3. The measuring sensor according to claim 1, wherein the sensor element is planar.

4. The measuring sensor according to claim 1,
    wherein the ceramic molded housing includes a sintered steatite ceramic, material,
    wherein a packet including the first compressing element, the seal element, and the second compressing element is compressed such that the packet fills at least one of the longitudinal hole and an interior of the metal shell, and wherein the packet terminates flush with at least one of the connector side of the ceramic molded housing and a connector side of the metal shell.

5. The measuring sensor according to claim 1, wherein the seal element includes at least one of a glass material and a metal material, and wherein the seal element is placed as one of a loose-poured powder, granules, and a compound.

6. The measuring sensor according to claim 5, wherein the metal material includes a copper material.

7. The measuring sensor according to claim 5, further comprising:

an organic binder that is added to one of the loose-poured powder, the granules, and the compound.

8. The measuring sensor according to claim 1, wherein the seal element includes at least one of a glass material and a metal material, and wherein the seal element is inserted as a compact.

9. The measuring sensor according to claim 8, wherein the metal material includes a copper material.

10. The measuring sensor according to claim 8, wherein the compact is presintered.

11. The measuring sensor according to claim 8, wherein the compact is a cast film.

12. The measuring sensor according to claim 1, wherein the first compressing element includes a temperature-resistant material with a predetermined frictional characteristic.

13. The measuring sensor according to claim 12, wherein the temperature-resistant material includes one of a steatite material, a talc material, a graphite material, a boron nitride material, a copper material, a glass material, a glass-ceramic material, and an oxide-ceramic material.

14. The measuring sensor according to claim 12, wherein the first compressing element is placed as one of a loose-poured powder and granules.

15. The measuring sensor according to claim 14, further comprising:

an organic binder that is added to one of the loose-poured powder and the granules.

16. The measuring sensor according to claim 12, wherein the first compressing element is placed as a compact.

17. The measuring sensor according to claim 16, wherein the compact is presintered.

18. The measuring sensor according to claim 12, wherein the first compressing element is placed as a cast film.

19. The measuring sensor according to claim 12, wherein the first compressing element is inserted cold to fix initially the sensor element.

20. The measuring sensor according to claim 1, wherein the second compressing element includes one of a steatite material and a talc material.

21. The measuring sensor according to claim 1, wherein the second compressing element includes one of a ceramic material, a zirconium dioxide, a Ba-Al silicate glass, and at least one of a high-melting glass and a metal powder.

22. The measuring sensor according to claim 20, wherein the second compressing element has an approximately plane end surface disposed on the measuring-gas side.

23. The measuring sensor according to claim 21, wherein the second compressing element has an approximately plane end surface disposed on the measuring-gas side.

24. The measuring sensor according to claim 21, wherein an end surface of the second compressing element exhibits projections extending to the seal element, the projections anchoring the second compressing element into the seal element.

25. The measuring sensor according to claim 24, wherein the projections extend approximately parallel to side surfaces of the sensor element.

26. The measuring sensor according to claim 20, further comprising:

at least one of an organic binder that is added to the second compressing element and a compacting aid that is added to the second compressing element.

27. The measuring sensor according to claim 26, wherein the second compressing element is not presintered.

28. The measuring sensor according to claim 21, wherein the second compressing element is presintered.

29. A method for fabricating a measuring sensor, comprising the steps of:

forming a workpiece by performing the steps of:
inserting a first compressing element into one of a longitudinal hole of a ceramic molded housing provided with an inserted sensor element and a metal shell provided with the inserted sensor element and pushed on the ceramic molded housing,
laying a seal element on the first compressing element and around the sensor element, and
laying a second compressing element on the seal element;

placing the workpiece in a temperature-resistant workpiece carrier;

heating the workpiece carrier and the workpiece in a furnace to a first temperature for a length of time;

removing the workpiece carrier from the furnace; and via an external ram, inserting at a second temperature the second compressing element, while warm, onto and into the seal element inside one of the longitudinal hole and the metal shell, until the external ram makes contact with at least one of the ceramic molded housing and the metal shell.

30. The method according to claim 29, wherein the step of heating the workpiece carrier in the furnace includes the step of heating the workpiece carrier in an air atmosphere.

31. The method according to claim 29, wherein the step of inserting the second compressing element includes the step of inserting the second compressing element in an air atmosphere.

32. The method according to claim 29, wherein the step of inserting the first compressing element includes the step of inserting the first compressing element cold, the first compressing element including a powder compact.

33. The method according to claim 29, wherein the step of inserting the first compressing element includes the step of inserting the first compressing element warm, the first compressing element including a presintered powder compact.

34. The method according to claim 29, wherein the step of inserting the first compressing element includes the step of inserting the first compressing element cold, the first compressing element including a cast film.

35. The method according to claim 34, wherein the cast film includes an organic binder, the organic binder being filled with at least one of a ceramic powder, a high-melting glass, a graphite, a boron nitride, a temperature-resistant metal powder, a film reinforced with fibers, and a film reinforced with fabric.

36. The method according to claim 35, wherein the ceramic powder includes at least one of $Al_2O_3$ and $ZrO_2$.

37. The method according to claim 35, wherein the temperature-resistant metal powder includes a Cu material.

38. The method according to claim 29, wherein the step of laying the seal element includes the step of laying the seal element as a preformed, one-piece glass-Cu compound compact.

39. The method according to claim 29,
wherein the step of laying the seal element on the first compressing element includes the step of inserting a first component of the seal element as a preformed compact of Cu powder and then inserting a second component of the seal element as a Li-borosilicate glass compact, and
wherein the step of inserting the second compressing element includes the step of causing the Li-borosilicate glass compact of the second component to penetrate into the preformed compact of Cu powder of the first component.

40. The method according to claim 29, wherein the step of heating the workpiece carrier in the furnace to the first temperature for the length of time includes the step of heating the workpiece carrier to approximately 850° C. for approximately 15 minutes.

41. The method according to claim 29, wherein the step of inserting the second compressing element includes the step of inserting the second compressing element unsintered as a steatite compressing element with a 2% organic binder.

42. The method according to claim 29, wherein the step of inserting the second compressing element includes the step of inserting the second compressing element as a steatite compact presintered at 600° C. for two hours with an addition of an organic binder.

43. The method according to claim 29, wherein the step of inserting the second compressing element includes the step of inserting the second compressing element as a presintered $ZrO_2$ ceramic compact.

44. The method according to claim 29, wherein the step of inserting the second compressing element includes the step of anchoring the second compressing element into the seal element by penetrating the seal element via projections, the projections being disposed on an end face of the second compressing element facing the seal element.

45. The method according to claim 44, wherein the projections project parallel with the sensor element.

46. The method according to claim 29,
wherein the external ram is split, and
wherein a portion of the external ram includes one of a sintered $Al_2O_3$ ceramic and a $ZrO_2$ ceramic, the portion being set on the second compressing element and being co-heated to a joining temperature.

* * * * *